United States Patent [19]

Shanzer et al.

[11] Patent Number: 4,649,218

[45] Date of Patent: Mar. 10, 1987

[54] LIPOPHILIC LITHIUM IONOPHORES

[75] Inventors: Abraham Shanzer, Bat Yam; David Samuel, Rehovot, both of Israel

[73] Assignee: Yeda Research and Development Company Ltd., Rehovot, Israel

[21] Appl. No.: 225,043

[22] Filed: Jan. 14, 1981

[30] Foreign Application Priority Data

Jan. 17, 1980 [IL] Israel .......................................... 59148

[51] Int. Cl.$^4$ ........................................... C07C 103/38
[52] U.S. Cl. .................................... 564/197; 560/169; 562/564; 540/454
[58] Field of Search ................ 564/203, 197; 424/320; 560/169; 260/239 R; 562/564

[56] References Cited

U.S. PATENT DOCUMENTS 3,699,165  10/1972  Albers et al. ........................ 564/203

OTHER PUBLICATIONS

Olsher et al., J. Am. Chem. Soc., vol. 102, No. 10, pp. 3338–3345 (1980).
Kirsh et al., Helv. Chim. Acta., vol. 60, No. 7, pp. 2326–2333 (1977).
Kirsch et al., Helv. Chim. Acta., vol. 61, No. 6, pp. 2019–2039 (1978).

*Primary Examiner*—Nicky Chan
*Attorney, Agent, or Firm*—Browdy and Neimark

[57] ABSTRACT

The present inveniton relates to novel lithium ionophores, to a process for producing such lithium ionophores and to their uses as pharmaceutical compositions, electrodes and as components of batteries.

4 Claims, No Drawings

LIPOPHILIC LITHIUM IONOPHORES

FIELD OF THE INVENTION

The present invention relates to novel lithium ionophores, to the production of these and to pharmaceutical compositions containing same as active ingredients.

The novel ionophores are useful in therapy where lithium is to be administered, and especially in the treatment of manic-depression and similar syndromes. They may also be used for the separation and enrichment of lithium ion and isotopes and in the design of lithium selective membranes in ion selective electrodes and of lithium batteries.

BACKGROUND OF THE INVENTION

Lithium ions have been found to be effective agents for the treatment of bipolar manic-depression. Lithium is also fairly effective as prophylactic for some forms of monopolar depression and is used nowadays in the treatment of a very large number of patients all over the world. The mode of action of lithium is not adequately understood.

The major shortcomings of the "lithium therapy" are the large dosages required (of the order of some grams per day) and the delayed onset of the effect. Both disadvantages are due to the slow penetration of lithium through the blood brain barrier and through other hydrophobic layers and membranes of the central nervous system. The high dosages necessary causes lithium build-up in organs such as the liver, kidneys and in the thyroid, resulting in effects such as thirst, gain of weight and thyroidal disorders.

SUMMARY OF THE INVENTION

According to the present invention there are provided novel lithium ionophores, which are useful as active ingredients of pharmaceutical compositions. The novel ionophores enhance the uptake of lithium into the brain and other tissues resulting in a rapid onset of action and reducing the doses necessary. This is a very pronounced advantage, as in cases of manic-depression the danger of self-injury and of suicide of the patient is quite high during the first days of the disease, and as the large doses and various other drugs that must be used result in unfavorable side effects.

It has been found that the rate of penetration of lithium into the brain, when administered together with the lithium ionophore of the present invention is significantly greater than the rate of penetration of lithium itself after intraventricular, intraperitoneal or intravenous injections. The latter mode of administration may be used with humans and the application per os also seems feasible.

The present invention relates to the novel lithium ionophores and to the process for their production. The invention further relates to such lithium ionophores linked to macromolecules adapted to modify the delivery of the lithium to specific organs and also to such ionophores linked to suitable antibodies or parts thereof which result in the delivery of the lithium to predesignated targets in the human body.

The process of production of the novel lithium ionophores comprises three alternative routes (Chart I).

The first route (Route a) involves condensing a stannoxane I with a suitable alkyl bromo acylamide resulting in the intermediate II, wherein $R^1$ and $R^2$ are alkyl groups of 1 to 3 carbon atoms, and $R^3$ and $R^4$ are alkyl groups of 1 to 2 carbon atoms including interlinked systems where $R^3$ is attached to $R^4$, $-R^3-R^4-$. This intermediate II is then alkylated with an organic bromide to result in a product III, which is further treated to introduce the desired lithium salt.

Lithium is introduced by dissolving the ionophore in a suitable solvent, and an excess of lithium salt is added. The mixture is heated, left to stand overnight, filtered and concentrated to give the desired product.

Another process for preparing the ionophore lithium complex comprises dissolving lithium-perchlorate in ethanol, adding a solution of the ionophore in ethanol in an equimolar ratio, stirring overnight and evaporating off the ethanol.

The second route (Route b) involves preparation of the desired secondary amine IV by one of three alternative methods: alkylation of a primary amine with a halide, addition of a primary amine to an olefin or acylation of a primary amine with an acyl halide and subsequent reduction with lithium aluminum hydride. Once prepared, the secondary amine IV is condensed with a diacyl dihalide V to produce product III.

The third route (Route c) involves modification of product III to a derivative III'.

A process for the preparation of the lithium ionophores of the present invention according to Route a comprises condensing a stannoxane of Formula I with a suitable alkyl bromoacyl amide resulting in an intermediate of the Formula II and reacting same with a suitable agent to introduce a suitable hydrophilic residue X or Y containing $-O-$, $-\underset{\underset{O}{\|}}{C}-$, $-\underset{\underset{O}{\|}}{C}-O-$, $-\underset{\underset{O}{\|}}{C}-N-$ moieties.

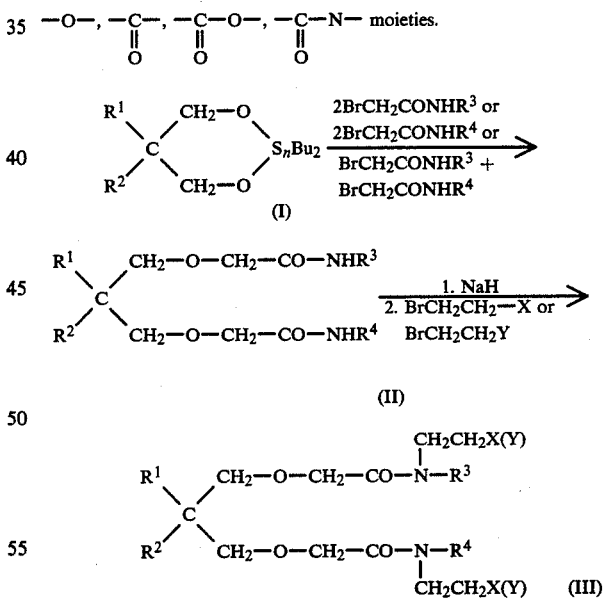

wherein when 2 $BrCH_2CONHR^3$ or 2 $BrCH_2CONHR^4$ are used, there are obtained compounds wherein in the first case there are two substituents $R^3$, and in the second case there are two substituents $R^4$; and when there are used one after the other reactants $BrCH_2CONHR^3$ and $BrCH_2CONHR^4$, there are obtained compounds wherein there are present both $R^3$ and $R^4$ as shown in the above formula, wherein X and Y, which may be identical or different, each represents a group selected from $-R^5-O-R^6$, $-R^5-\underset{\underset{O}{\|}}{C}-R^6-$, $-R^5-\underset{\underset{O}{\|}}{C}-O-R^6-$ and $-R^5-\underset{\underset{O}{\|}}{C}-N(R^6)_2$ wherein $R^1$ and $R^2$ are each alkyl groups, including cycloalkyl;

$R^3$, $R^4$, $R^5$ and $R^6$ are alkyl groups of 1 to 12 carbon atoms including cases where $R^3$ and $R^4$ are interlinked, $R^3-R^4$; and wherein $R^6$ can also designate a hydrogen atom; and wherein $R^5$ can be a bond.

PREPARATION OF IONOPHORE

Example 1

Preparation of Ionophore AS 701

The ionophore defined as Ionophore AS 701 was prepared as follows according to Route a.

To a solution of 4 ml ($1.48 \times 10^{-2}$ mol) dibutyl tin diethoxide in 60 ml toluene there were added 1.54 g ($1.48 \times 10^{-2}$ mol) 2,2-dimethyl-1,3-dihydroxypropane and the reaction mixture was refluxed overnight with concurrent removal of ethanol as binary azeotrope. A quantity of 6.95 g ($2.96 \times 10^{-2}$ mol) N-heptyl-bromoacetamide and 0.8 ml pyridine was added and reflux was continued for a further 2 hours. The crude reaction mixture was filtered, concentrated and subjected to chromatography on silica gel to provide the diamide. A quantity of 502 mg ($1.2 \times 10^{-3}$ mol) diamide in 25 ml benzene was treated with 170 mg ($1.2 \times 10^{-3}$ mol) sodium hydride (dispersion in oil), the mixture was heated to reflux under nitrogen and 0.405 ml 1-bromoethylether was added and heating was continued for a further 7 hours. Excess sodium hydride was destroyed by the addition of 95% ethanol and water, the organic layer was separated, washed and dried and subsequently concentrated in vacuo to give an oily residue. Chromatography of the residue on silica gel gave the pure tetraether, N,N'-diheptyl-5,5-dimethyl-N,N'-di(2-oxapentyl)-3,7-dioxanonane diamide, as an oil.

The lithium ion was incorporated into the ionophore AS 701 by dissolving the ionophore in chloroform, adding excess of lithium salt, and short heating up of the mixture. The resulting suspension was allowed to stand overnight at room temperature, filtered and concentrated to provide the syrup like complex as residue. Alternatively 83 mg of ionophore AS 701 were dissolved in minimal amount ethanol, a solution of 1.0 mg $LiClO_4$ in methanol added and the mixture heated. After standing overnight at room temperature, the mixture was concentrated to provide as residue the oily lithium-ionophore complex.

Example 2

Preparation of Ionophore AS 702

The ionophore defind as Ionophore AS 702 was prepared as follows according to Route b.

Preparation of N-heptyl-3-aminopropionyl ethyl ester IV ($R^3 = C_7H_{15}$, $X = COOCH_2CH_3$)

An amount of 25 g (0.25 mol) ethyl acrylate was dissolved in 50 ml ethanol, cooled to $-60°$ C. and treated dropwise with 37 ml (0.25 mol) heptylamine. The reaction mixture was then allowed to warm up slowly to room temperature and stirring continued for two days. Subsequent concentration of the mixture and distillation in vacuo provided the amino ester IV as colorless oil. 29.7 g (0.21 mol), b.p. $81°-83°$ C./17 mm Hg. nmr ($CDCl_3$) $\delta 4.0$ (q, 2H, $-OCH_2-$), 2.6 (m, 6H, $-NCH_2CH_2CO$ and $-NCH_2-$) and 0.8-1.4 ppm (m, 16H, aliphatic hydrogens).

Preparation of N,N'-diheptyl-5,5-dimethyl-N,N'-di-[3(ethyl propionato)]-3,7-dioxanonane diamide (III) ($R^1 = R^2 = CH_3-$, $R^3 = R^4 = C_7H_{15}-$, $X = Y = COOCH_2CH_3$)

A quantity of 2 ml ($9.3 \times 10^{-3}$ mol) diacyl dichloride V were dissolved in dry methylene chloride and treated dropwise at $-5°$ C. with 2.52 g ($1.8 \times 10^{-2}$ mol) of the amino ester IV. The mixture was then allowed to warm up to room temperature and stirring continued for 24 hours. Concentration of the reaction mixture in vacuo and chromatography of the residue on silica gel provided the diester III. 4.56 g ($7.4 \times 10^{-3}$ mol).

Example 3

Preparation of Ionophore AS 703

The ionophore defined as Ionophore AS 703 was prepared as follows according to Route c.

Preparation of N,N'-diheptyl-5,5-dimethyl-N,N'-di-[3-propioanato]-3,7-dioxanonane diamide (III) ($R^1 = R^2 = CH_3-$, $R^3 = R^4 = C_7H_{15}-$, $X = Y' = COOH$)

Diester III, 13.05 g ($2.12 \times 10^{-2}$ mol) were dissolved in 150 ml ethanol and treated with 50 ml of a saturated aqueous solution of $K_2CO_3$ under reflux overnight. The two phases separated, the water layer was removed, acidified with diluted HCl, extracted with ether and the ether phase washed with water. Concentration in vacuo and chromatography of the residue on silica gel provided the diacid III', 10.54 g ($1.89 \times 10^{-2}$ mol).

The following Table illustrates a number of compounds of the present invention, which were prepared in an analogous manner:

$$R^1 \underset{R^2}{\diagdown} C \underset{CH_2-O-CH_2-CO-N-R^4}{\overset{CH_2-O-CH_2-CO-N-R^3}{\diagup}} \begin{array}{c} CH_2CH_2X(Y) \\ | \\ \\ | \\ CH_2CH_2X(Y) \end{array}$$

wherein the substituents are:

TABLE

| | | | Examples 4 to 10: | | | |
|---|---|---|---|---|---|---|
| No. of Example | $R^1$ | $R^2$ | $R^3$ | $R^4$ | X | Code |
| 4 | $CH_3$ | $CH_3$ | $C_7H_{15}$ | $C_7H_{15}$ | H | AS 698 |
| 5 | $CH_3$ | $CH_3$ | $CH_3$ | $CH_3$ | $CH_3$ | AS 699 |

TABLE-continued

| | | | | | | |
|---|---|---|---|---|---|---|
| 6 | CH$_3$ | CH$_3$ | C$_7$H$_{15}$ | C$_7$H$_{15}$ | CH$_2$CH$_2$CON(CH$_2$CH$_3$)$_2$ | AS 704 |
| 7 | CH$_3$ | CH$_3$ | C$_2$H$_5$ | C$_2$H$_5$ | CH$_2$CH$_2$COOCH$_2$CH$_3$ | AS 700 |
| 8 | HO.CH$_2$ | HO.CH$_2$ | C$_7$H$_{15}$ | C$_7$H$_{15}$ | CH$_2$CH$_2$OCH$_2$CH$_3$ | AS 705 |
| 9 | CH$_3$ | CH$_3$ | C$_7$H$_{15}$ | C$_7$H$_{15}$ | C$_5$H$_9$O | AS 706 |
| 10 | CH$_3$ | CH$_3$ | C$_{12}$H$_{25}$ | C$_{12}$H$_{15}$ | CH$_2$CH$_2$OCH$_2$CH$_3$ | AS 707 |

IR SPECTRA OF IONOPHORES (NEAT)

| CODE | NH | IR- SPECTRA (cm$^{-1}$) CO | COC |
|---|---|---|---|
| AS 698 | 3320 | 1660 / 1540 | 1130 |
| AS 700 | | 1730 / 1640 | 1110 / 1140 |
| AS 701 | | 1650 / 1465 | 1115 |
| AS 702 | | 1735 / 1645 | 1110 / 1140 |
| AS 703 | | | |
| AS 704 | | 1640 / 1460 | 1110 |

Preferred compounds are of the following formula:

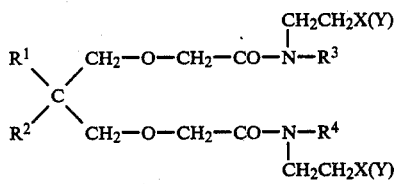

wherein X and Y may be identical or different, designating: —OCH$_2$CH$_3$, —COOCH$_2$CH$_3$, —COOH, —CON(CH$_2$CH$_3$)$_2$.

Preferred alkyl groups are as follows:

R$^1$ and R$^2$: alkyl of from 1 to 3 carbon atoms, including cycloalkyl;

R$^3$ and R$^4$: alkyl of from 1 to 12 carbon atoms, including cases where R$^3$ and R$^4$ are interlinked to —R$^3$—R$^4$—.

The novel ionophore lithium complexes were tested in rats by intraventricular injections, by injection into the tail vein and by interperitoneal injections, and the distribution of lithium into the various areas of the brain was determined after 20 hours. Rats injected with the same quantity of lithium chloride or other salts were used as controls. The concentration of lithium per mg tissue was determined by measurement of atomic absorption. After intracerebral injection the ratio of lithium in the two sets of experiments was: 2.99 in the cortex; 2.35 in the caudate; 3.9 in the hippocampus; and about 1.39 in the brain stem.

After injection into the rat tail or interperitoneally the ratios in various brain areas were also higher when the lithium ionophore complex was used as compared to lithium salts at the same molar concentration.

The novel lithium ionophores may also be applied in other areas, which involve lithium separation, isotope enrichment or solubilization.

Lithium can be extracted from sea water, salt brines or industrial wastes by means of selective lithium ionophores dissolved in an organic solvent or attached to a membrane or resin.

The stable isotopes of lithium, $^6$Li and $^7$Li can be differentially enriched by means of a chemical exchange reaction:

$$^6Li(aq.) + {}^7Li(ionophore) \rightarrow {}^6Li(ionophore) + {}^7Li(aq.)$$

utilizing an aqueous solution of lithium and an organic phase of ionophore.

This technique has been used successfully for separating isotopes of calcium and titanium. Using lipophilic lithium ionophores, the isotopes can be separated by countercurrent distribution or cyclic systems, using an aqueous solution of lithium and a water immiscible solution (such as chloroform, methylenechloride or pentane) of the ionophore.

Lithium ionophores can also be utilized in ion selective electrodes in which an ionophore is embedded or attached to a membrane or an inert matrix, which seals an internal reference electrode. The concentration of lithium ions in water or biological fluids can be determined by means of the change of the reference electrode potential.

Lithium ionophores may also be used as additives to improve lithium batteries that are based on lithium electrodes, an inorganic solvent and an inert electrolyte. The use of lithium ionophores is believed to reduce the resistance and enhance the conductivity of the battery, by improving the solubility of the lithium chloride in the solvent.

CHART I

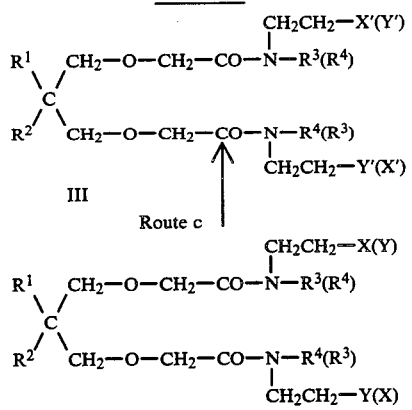

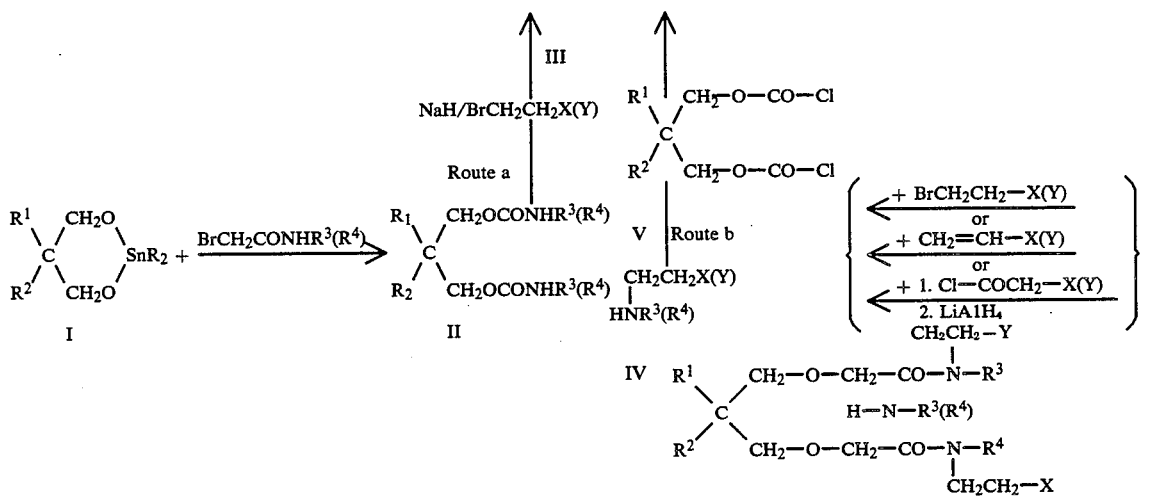

wherein:
R is alkyl or aryl;
$R^1$ and $R^2$ are each alkyl groups, including cycloalkyl;
$R^3$ and $R^4$ are each alkyl groups of 1 to 12 carbon atoms, including residues wherein $R^3$ and $R^4$ are interlinked, —$R^3$—$R^4$—;
X and Y, which may be identical or different, each represents a group selected from:

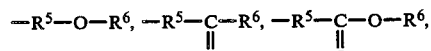

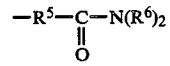

wherein $R^5$ and $R^6$ are each alkyl groups, wherein $R^5$ may also be zero and $R^6$ may also be H. Also $R^5$—O—$R^6$ may be cyclic.

We claim:
1. A lithium ionophore of the formula wherein
X and Y, which may be identical or different, are each a group selected from:

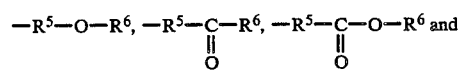

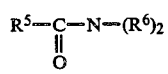

wherein
$R^1$ and $R^2$ are alkyl groups of 1 to 3 carbon atoms,
$R^3$, $R^4$, $R^5$ and $R^6$ are alkyl groups of 1 to 12 carbon atoms,
wherein
$R^6$ can also be hydrogen,
wherein
$R^3$ and $R^4$ can be interlinked to form a group, —$R^3$—$R^4$—
and wherein
$R^5$ may also be a bond.

2. A lithium ionophore according to claim 1, wherein X and Y each designates a group —$(CH_2)_m$—O—$(CH_2)_n$—$CH_3$, wherein m and n are integers from 0 to 7.

3. A lithium ionophore according to claim 2, wherein m is 0 and n is 2.

4. A lithium-lithium ionophore complex comprising lithium complexed with the lithium ionophore of claim 1.

* * * * *